(12) United States Patent
Wang et al.

(10) Patent No.: US 11,707,390 B2
(45) Date of Patent: Jul. 25, 2023

(54) ABSORBENT ARTICLES HAVING A SECONDARY TOPSHEET

(71) Applicant: The Procter & Gamble Company, Cincinnati, OH (US)

(72) Inventors: Fancheng Wang, Beijing (CN); Tong Jia, Beijing (CN); Xiaoxin Liu, Beijing (CN); Zifang An, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 516 days.

(21) Appl. No.: 16/043,207

(22) Filed: Jul. 24, 2018

(65) Prior Publication Data
US 2019/0021917 A1 Jan. 24, 2019

(30) Foreign Application Priority Data
Jul. 24, 2017 (WO) ................ PCT/CN2017/094047

(51) Int. Cl.
*A61F 13/512* (2006.01)
*A61F 13/511* (2006.01)
(Continued)

(52) U.S. Cl.
CPC ........ *A61F 13/5123* (2013.01); *A61F 13/512* (2013.01); *A61F 13/5116* (2013.01);
(Continued)

(58) Field of Classification Search
CPC .............. A61F 13/5123; A61F 13/5116; A61F 13/512; A61F 2013/51019; A61F 2013/51021; A61F 2013/51026; A61F 2013/51066; A61F 2013/5127; A61L 15/24; A61L 15/26; A61L 15/28; A61L 15/425
See application file for complete search history.

(56) References Cited

U.S. PATENT DOCUMENTS

| | | |
|---|---|---|
| 4,321,924 A | 3/1982 | Ahr |
| 4,425,130 A | 1/1984 | DesMarais |
| (Continued) | | |

FOREIGN PATENT DOCUMENTS

| | | |
|---|---|---|
| CN | 201019925 Y | 2/2008 |
| CN | 101433484 A | 5/2009 |
| (Continued) | | |

OTHER PUBLICATIONS

International Search Report and Written Opinion; Application Ser. No. PCT/CN2017/094047; dated Oct. 16, 2019; 5 pages.
(Continued)

*Primary Examiner* — Jacqueline F Stephens
(74) *Attorney, Agent, or Firm* — Melissa G. Krasovec; George Henry Leal

(57) ABSTRACT

An absorbent article having a liquid permeable topsheet, a liquid impermeable sheet, an absorbent core disposed between the topsheet and the backsheet, and a secondary topsheet disposed between the topsheet and the absorbent core is described. The secondary topsheet has a first layer and a second layer. The first layer is located between the topsheet and the second layer, and a mean pore size of the first layer is larger than a mean pore size of the topsheet.

19 Claims, 8 Drawing Sheets

(51) Int. Cl.
*A61L 15/28* (2006.01)
*A61L 15/24* (2006.01)
*A61L 15/26* (2006.01)
*A61L 15/42* (2006.01)
*A61F 13/51* (2006.01)

(52) U.S. Cl.
CPC .............. *A61L 15/24* (2013.01); *A61L 15/26* (2013.01); *A61L 15/28* (2013.01); *A61L 15/425* (2013.01); *A61F 2013/51019* (2013.01); *A61F 2013/51021* (2013.01); *A61F 2013/51026* (2013.01); *A61F 2013/5127* (2013.01); *A61F 2013/51033* (2013.01)

(56) References Cited

U.S. PATENT DOCUMENTS

| | | | |
|---|---|---|---|
| 4,589,876 A | 5/1986 | Tilburg | |
| 4,950,264 A | 8/1990 | Osborn | |
| 5,520,673 A | 5/1996 | Yarbrough et al. | |
| 5,607,414 A * | 3/1997 | Richards | A61F 13/15203 604/378 |
| 5,810,796 A | 9/1998 | Kimura et al. | |
| 5,997,980 A | 12/1999 | Matoba et al. | |
| 6,060,638 A | 5/2000 | Paul et al. | |
| 6,566,578 B1 | 5/2003 | Glaug et al. | |
| 7,597,689 B2 | 10/2009 | Hoffmann et al. | |
| 8,344,202 B2 | 1/2013 | Schneider et al. | |
| 8,389,427 B2 | 3/2013 | Gustafsson et al. | |
| 2003/0220048 A1 | 11/2003 | Toro et al. | |
| 2004/0087924 A1 | 5/2004 | Sroda et al. | |
| 2005/0033253 A1 | 2/2005 | Fuchs et al. | |
| 2005/0136773 A1 | 6/2005 | Yahiaoui et al. | |
| 2006/0058762 A1 | 3/2006 | Yang et al. | |
| 2007/0100305 A1 | 5/2007 | Isogai et al. | |
| 2008/0113574 A1 | 5/2008 | Neron et al. | |
| 2008/0119806 A1 | 5/2008 | Nguyen | |
| 2012/0238978 A1 | 9/2012 | Weisman et al. | |
| 2014/0343523 A1 | 11/2014 | Viens et al. | |
| 2015/0351976 A1* | 12/2015 | Viens | D04H 1/425 604/378 |
| 2018/0200123 A1 | 7/2018 | Xie et al. | |

FOREIGN PATENT DOCUMENTS

| | | |
|---|---|---|
| CN | 104138310 A | 11/2014 |
| CN | 104323884 A | 2/2015 |
| CN | 104544730 A | 4/2015 |
| EP | 1776940 A1 | 4/2007 |
| EP | 2692321 | 2/2014 |
| JP | H10273884 A | 10/1998 |
| JP | 2005-041527 | 2/2005 |
| JP | 2008-018959 | 1/2008 |
| JP | 2008-106383 A | 5/2008 |
| JP | 4364247 | 11/2009 |
| JP | 5600539 | 10/2014 |
| WO | 2007034451 A1 | 3/2007 |

OTHER PUBLICATIONS

Search Report and Written Opinion for PCT/CN2017/094047 dated Mar. 6, 2018.
All Office Actions for U.S. Appl. No. 14/278,481.
All Office Actions for U.S. Appl. No. 14/731,802.

* cited by examiner

ABSORBENT ARTICLES HAVING A SECONDARY TOPSHEET

FIELD OF THE INVENTION

The present invention relates to absorbent articles comprising a liquid permeable topsheet, a liquid impermeable backsheet, a secondary topsheet disposed between the topsheet and the backsheet, and an absorbent core disposed between the secondary topsheet and the backsheet.

BACKGROUND OF THE INVENTION

Absorbent articles such as diapers and sanitary napkins are typically composed of multiple components such as a liquid-permeable topsheet, liquid-impermeable backsheet and a liquid-storing absorbent core disposed the topsheet and the backsheet, and it is desirable that body fluid on the topsheet sheet is easily drawn from the topsheet and promptly moves to the absorbent core without remaining in the topsheet.

It is desirable in an absorbent article that the body fluid discharged on the topsheet rapidly transfer from a top surface of the topsheet towards the bottom of the topsheet which usually keep in close contact with an absorbent core of the absorbent article, so that the body fluid rapidly transfers from the topsheet into the absorbent core without giving a wearer uncomfortable feeling of wetness.

Nonwovens including synthetic fibers formed from thermoplastic resin are widely used as topsheets constituting absorbent articles such as sanitary napkins, infant disposable diapers, personal care disposable diapers, and the like.

While various nonwovens have been suggested for use as a component such as topsheets for absorbent articles from the standpoints of skin sensation, a feeling of dryness, comfort, absorption of expelled bodily fluids, and prevention of fluid flow-back, consumers' interest in natural material has been increased, and absorbent articles having a topsheet made of a material containing cotton fibers were provided. Absorbent articles having a topsheet containing cotton fibers meet consumers' needs for materials of natural and gentle to the skin, however, the nature of cotton has inherent properties to hold fluid and spread the fluid on the topsheet before penetrating inside the absorbent article such as an absorbent core.

So as not to prevent liquid transfer from a topsheet to an absorbent core and minimize an amount of body fluid remaining on the topsheet, absorbent articles have been designed by incorporating one or more layers of material between a topsheet and an absorbent core.

Japanese Patent No. 4364247 discloses a disposable absorptive pad which includes a water-permeable topsheet facing the body side, an absorptive core and a second sheet placed between the topsheet and the absorptive core in which a fiber density on a side facing the absorptive core is higher than that on a side facing the topsheet.

Japanese Patent No. 5600539 discloses an absorbent article which inhibits absorbed bodily fluids from generating wetback onto a surface sheet, the absorbent article comprising a hydrophilic intermediate sheet lower in density than a surface sheet disposed between the surface sheet and an absorber.

In the art, it is common that the layer underneath topsheet has high capillary suction than that for topsheet. In case of 100% cotton topsheet or in some case cotton containing topsheet, it is very challenge to find material layers that can have high capillary suction than 100% cotton topsheet.

Therefore there is a continuous need for an absorbent article that provides the natural experience to consumers while it moves fluid fast and completely away from body.

There is a continuous need for an absorbent article with a topsheet containing natural fibers without compromising a fluid acquisition time.

There is also a continuous need for an absorbent article with a topsheet containing natural fibers which can reduce fluid-left in the topsheet.

SUMMARY OF THE INVENTION

The present invention provides an absorbent article comprising a liquid permeable topsheet, a liquid impermeable sheet, an absorbent core disposed between the topsheet and the backsheet, and a secondary topsheet disposed between the topsheet and the absorbent core, wherein the secondary topsheet comprises a first layer and a second layer, the first layer being located between the topsheet and the second layer, wherein a mean pore size of the first layer of the secondary topsheet is larger than a mean pore size of the topsheet. A mean pore size of the first layer of the secondary topsheet may be substantially equal to or larger than a mean pore size of the topsheet.

These and other features, aspects, and advantages of the present invention will become evident to those skilled in the art from a reading of the present disclosure.

DETAILED DESCRIPTION OF THE INVENTION

All ranges are inclusive and combinable. The number of significant digits conveys neither limitations on the indicated amounts nor on the accuracy of the measurements. All numerical amounts are understood to be modified by the word "about" unless otherwise specifically indicated.

The term "absorbent articles", as used herein, include disposable diapers, sanitary napkins, panty liners, incontinence pads, interlabial pads, breast-milk pads, sweat sheets, animal-use excreta handling articles, animal-use diapers, and the like.

The term "absorbent core", as used herein, refers to the component of the absorbent article that is primarily responsible for storing liquids. As such, the absorbent core typically does not include the topsheet or backsheet of the absorbent article.

The term "cellulose-based fibers", as used herein, intends to include both cellulose fibers such as pulp and cotton, and regenerated cellulose fiber such as rayon unless specified differently.

The term "component" of an absorbent article, as used herein, refers to an individual constituent of an absorbent article, such as a topsheet, acquisition layer, liquid handling layer, absorbent core or layers of absorbent cores, backsheets, and barriers such as barrier layers and barrier cuffs.

The term "joined", as used herein, refers to the condition where a first member is attached, or connected, to a second member either directly or indirectly. Where the first member is attached, or connected, to an intermediate member which in turn is attached, or connected, to the second member, the first member and second member are joined indirectly. The term "aperture", as used herein, refers to a hole. The apertures can either be punched cleanly through the web so that the material surrounding the aperture lies in the same plane as the web prior to the formation of the aperture (a "two dimensional" aperture), or holes formed in which at least some of the material surrounding the opening is pushed out of the plane of the web. In the latter case, the apertures may resemble a protrusion or depression with an aperture therein, and may be referred to herein as a "three dimensional" aperture, a subset of apertures.

As used herein, "hydrophilic" refers to a material or substance having affinity for water or aqueous fluids. In general, a hydrophilic surface will have a contact angle with water of less than 90° or less than 60°, or even less than 30°.

As used herein, the term "layer" refers to a three dimensional structure having two dimensions that are substantially greater than the third dimension. The term layer is not limited to single layers or sheets of material. Thus a layer may comprise laminates or combinations of several sheets or webs of the requisite type of materials. Accordingly, the term "layer" includes the terms "layers" and "layered."

Absorbent Article

Figure 1:
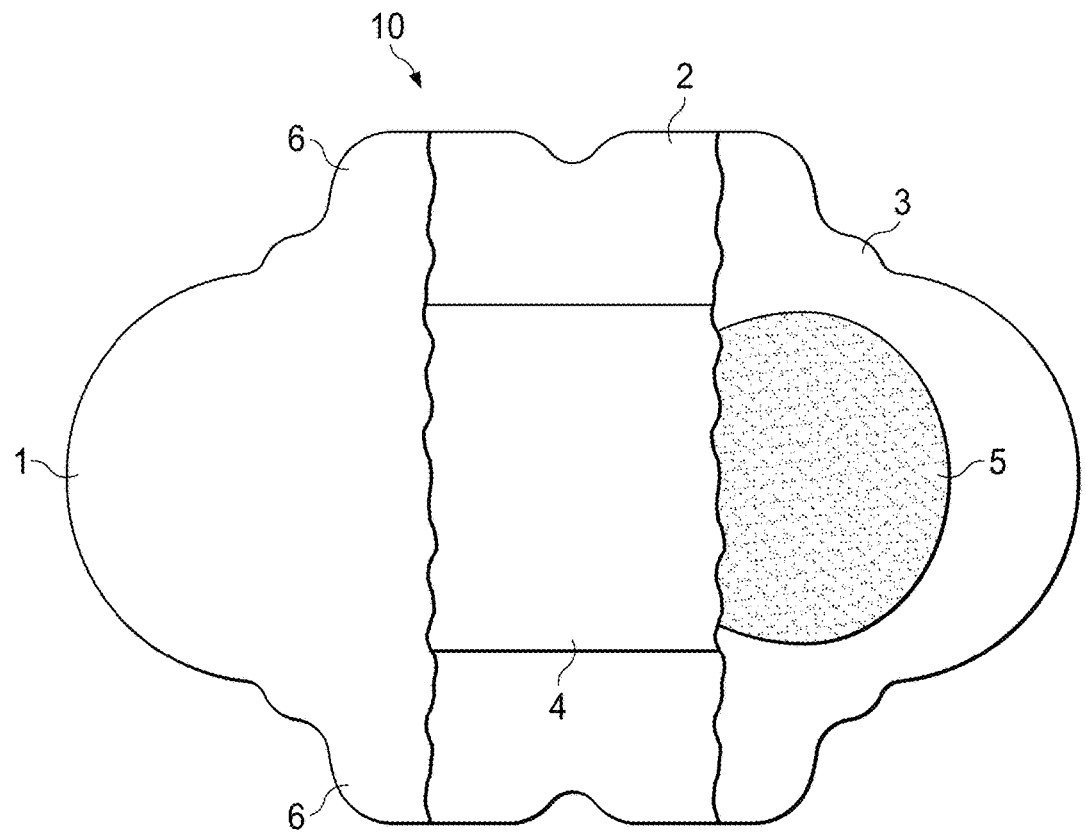
FIG. 1 is a plan view of an embodiment of an absorbent article according to the present invention.
Figure 2:
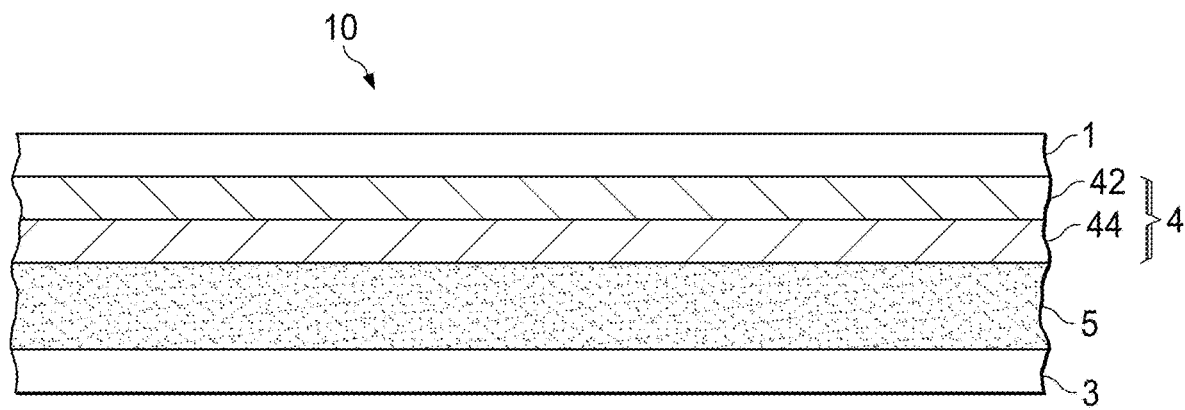
FIG. 2 is a partial cross section of an absorbent article of FIG. 1 in a transversal direction.

Referring to FIGS. 1 and 2, an absorbent article 10 according to the present invention comprises a liquid permeable topsheet 1, a liquid impermeable backsheet 3, and a secondary topsheet 4 disposed between the topsheet 1 and the backsheet 3. The absorbent article 10 may further comprise an absorbent core 3 disposed between the secondary topsheet 4 and the backsheet 3. The absorbent article 10 may further comprise sideflaps 6.

Still referring to FIGS. 1 and 2, the secondary topsheet 4 comprises a first layer 42 and a second layer 44, and the first layer 42 is located between topsheet 1 and the second layer 44 of the secondary topsheet 4.

Figure 3:
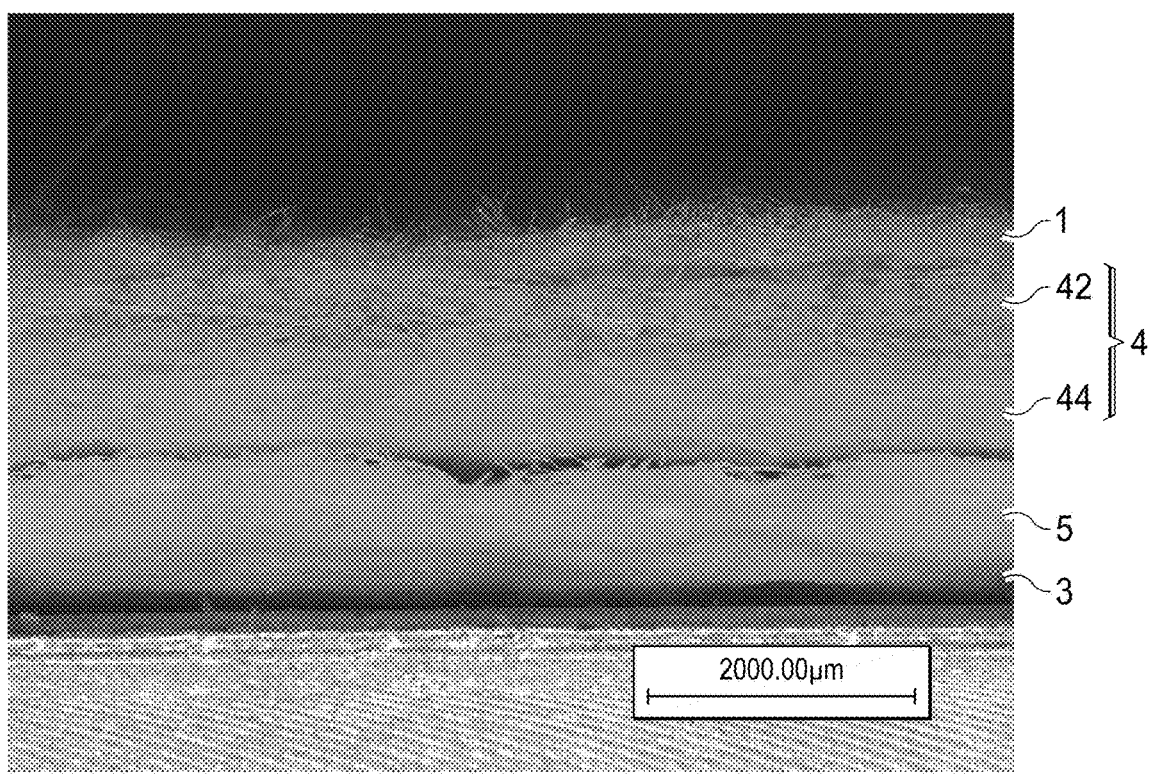
FIG. 3 is an electronic microscope image of a partial cross-section of an absorbent article of the present invention.
Figure 4:
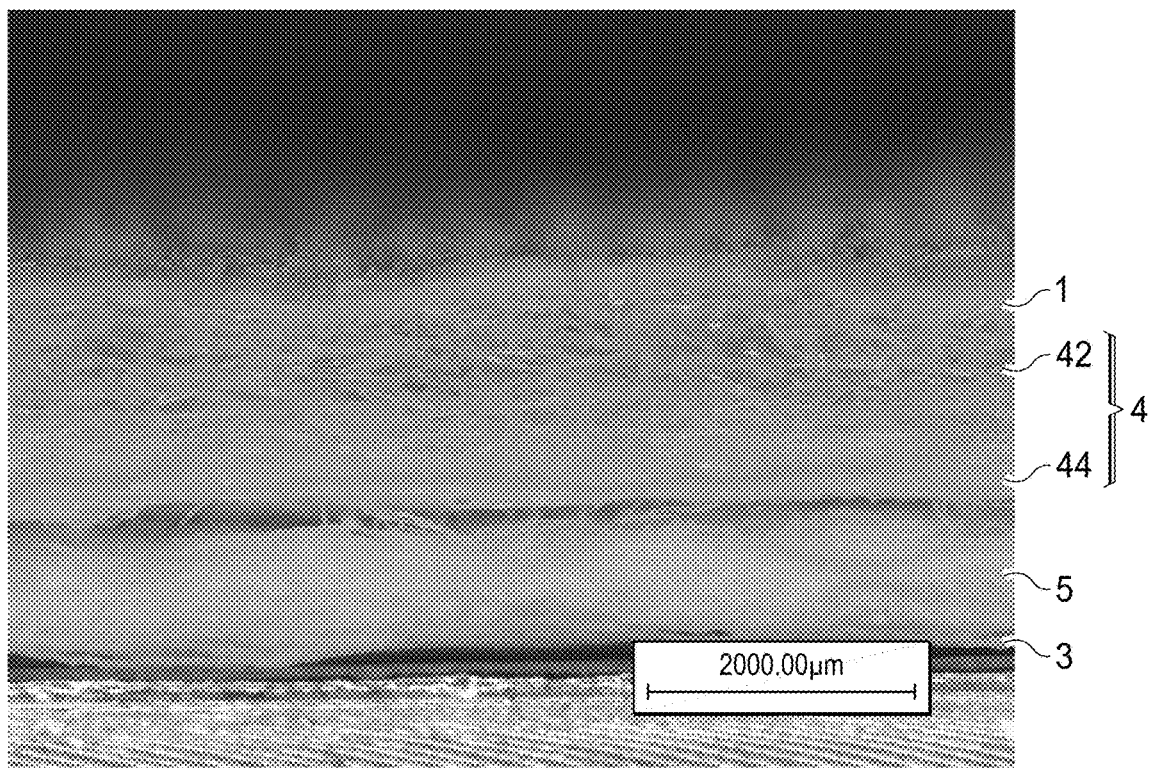
FIG. 4 is an electronic microscope image of a partial cross-section of an absorbent article of the present invention.
Figure 5:
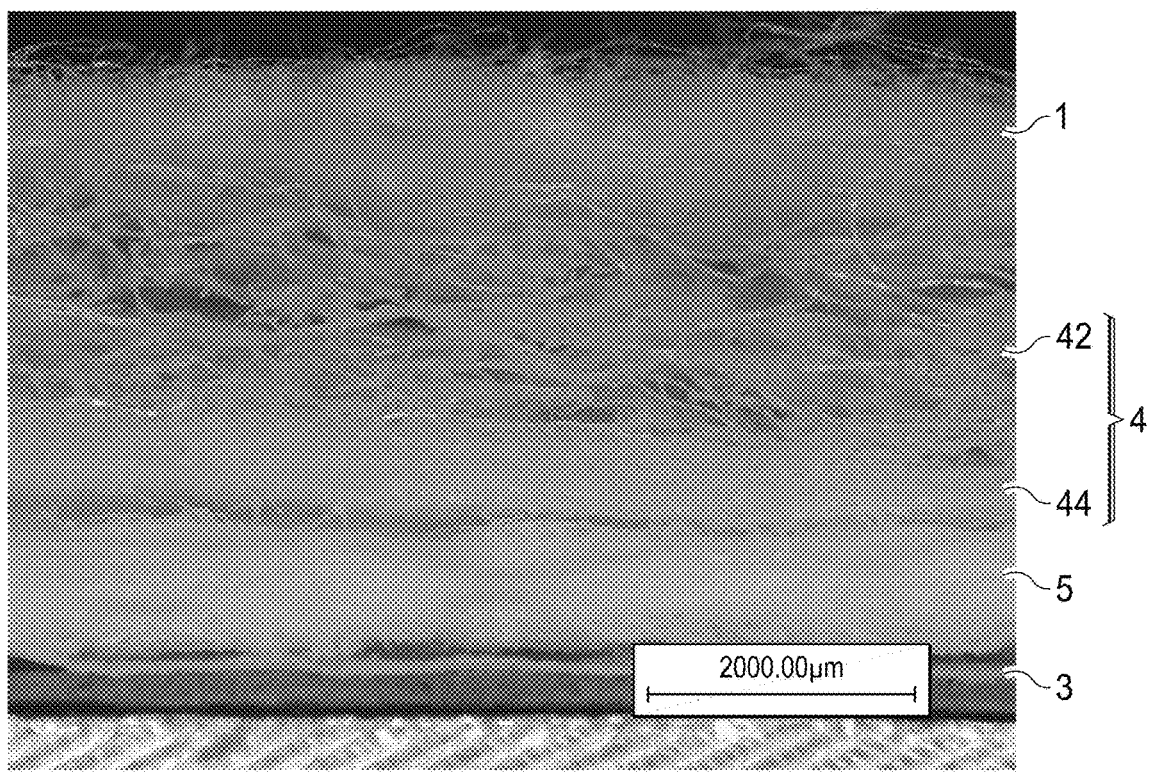
FIG. 5 is an electronic microscope image of a partial cross-section of an absorbent article of the present invention.
Figure 6:
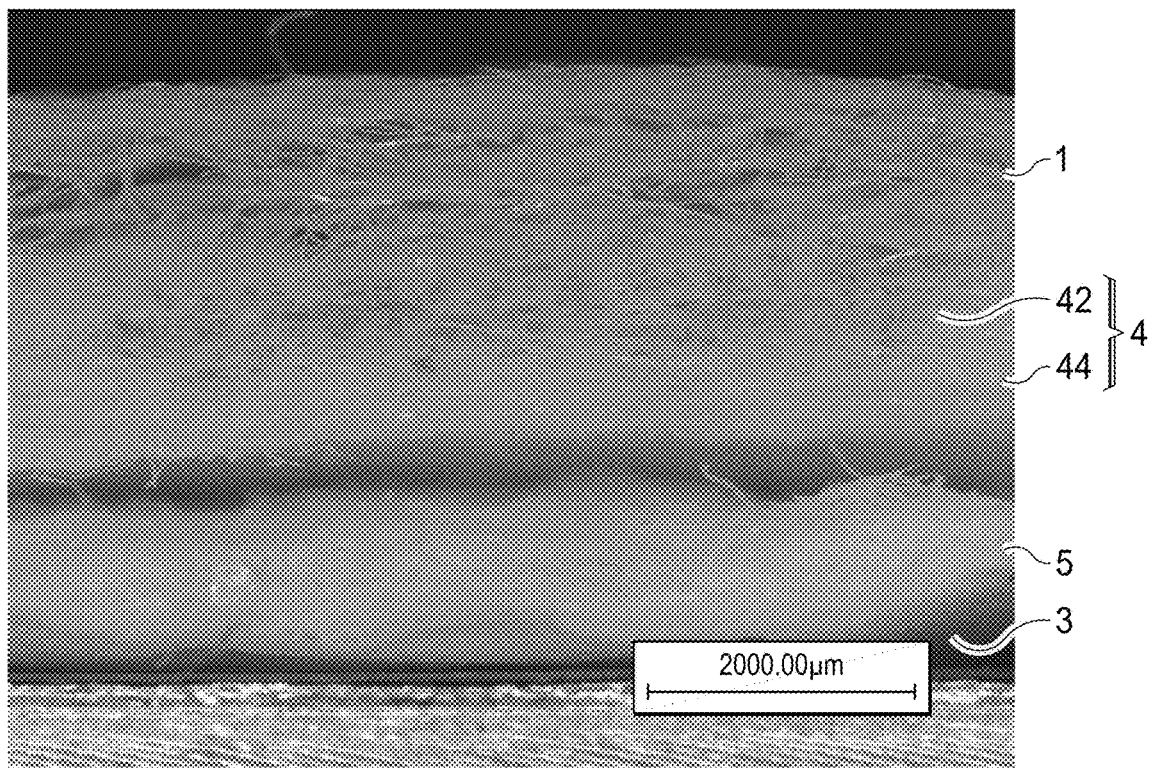
FIG. 6 is an electronic microscope image of a partial cross-section of an absorbent article of the present invention.
Figure 7:
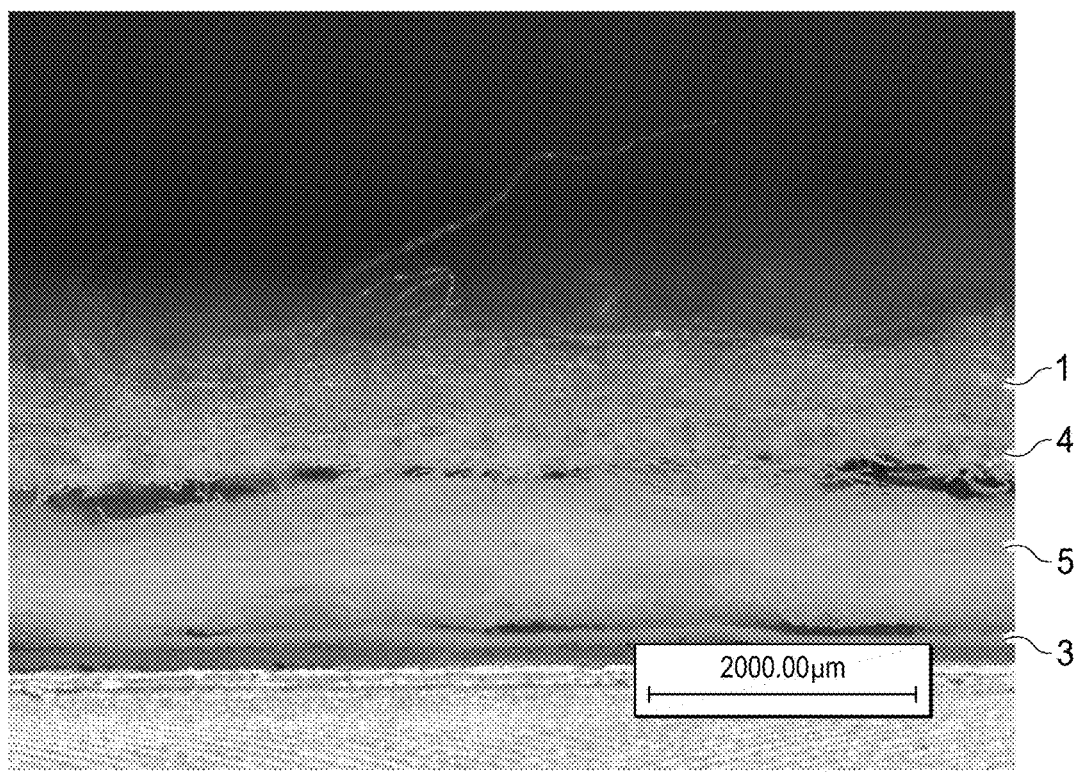
FIG. 7 is an electronic microscope image of a cross-section of a topsheet and a secondary topsheet in a comparative example.
Figure 8:
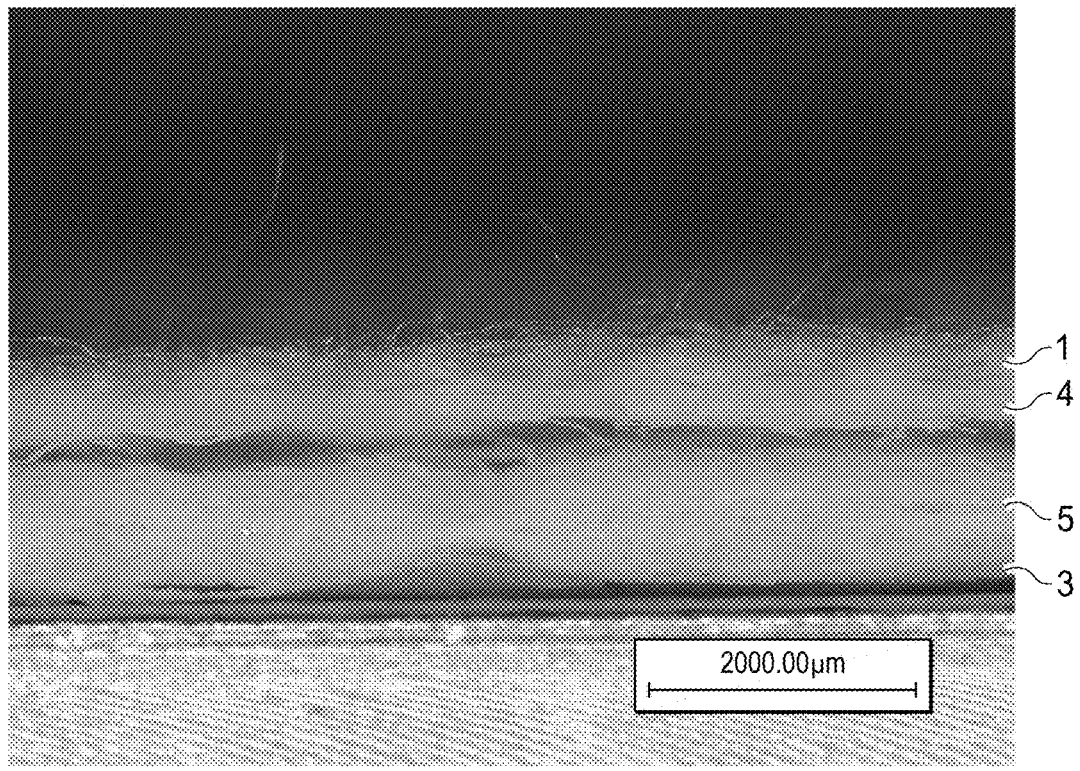
FIG. 8 is an electronic microscope image of a cross-section of a topsheet and a secondary topsheet in a comparative example.
Figure 9:
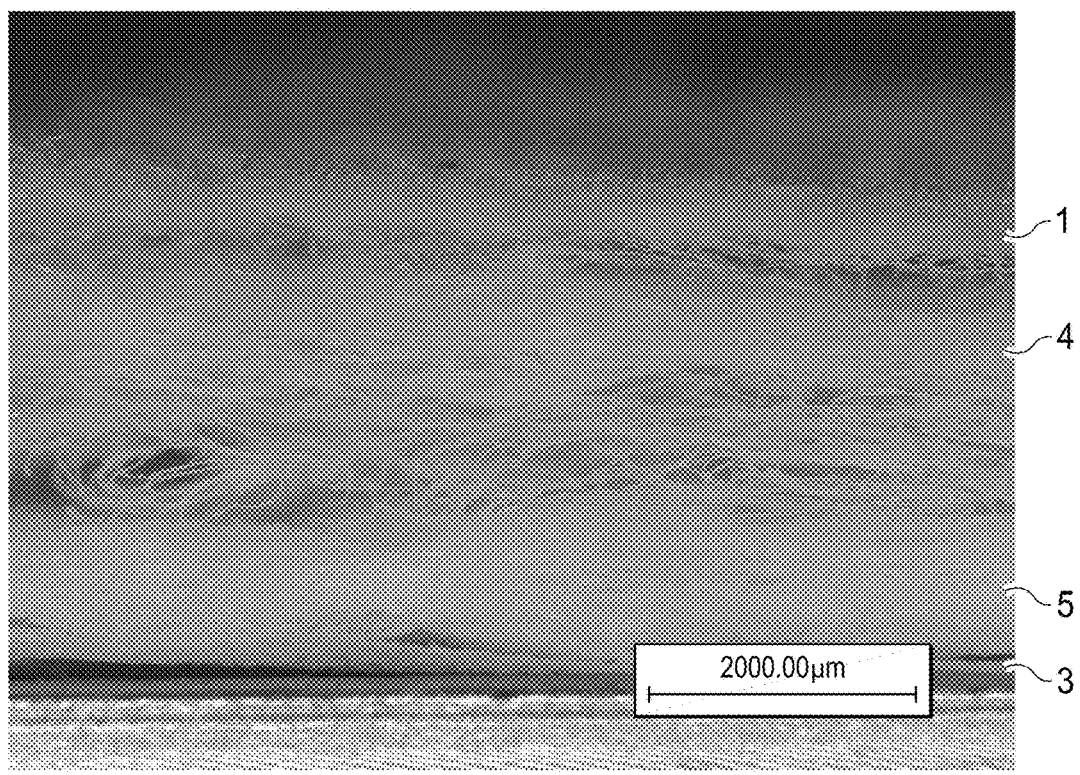
FIG. 9 is an electronic microscope image of a cross-section of a topsheet and a secondary topsheet in a comparative example.
Figure 10:
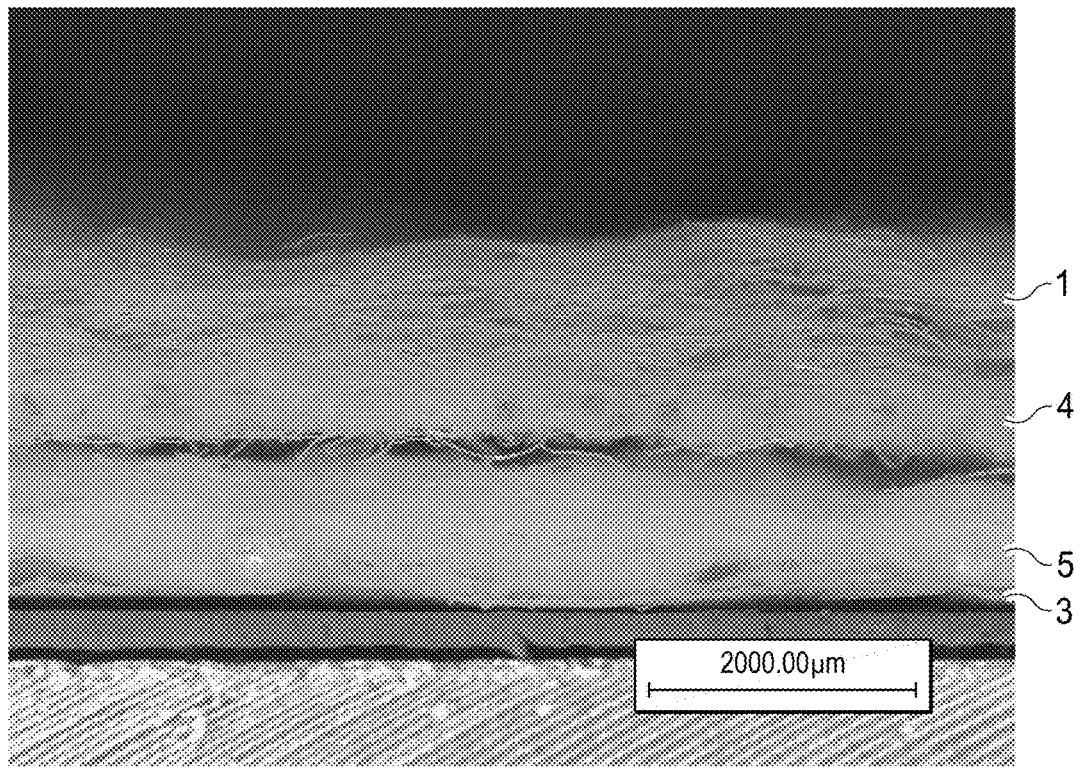
FIG. 10 is an electronic microscope image of a cross-section of a topsheet and a secondary topsheet in a comparative example.
Figure 11A:
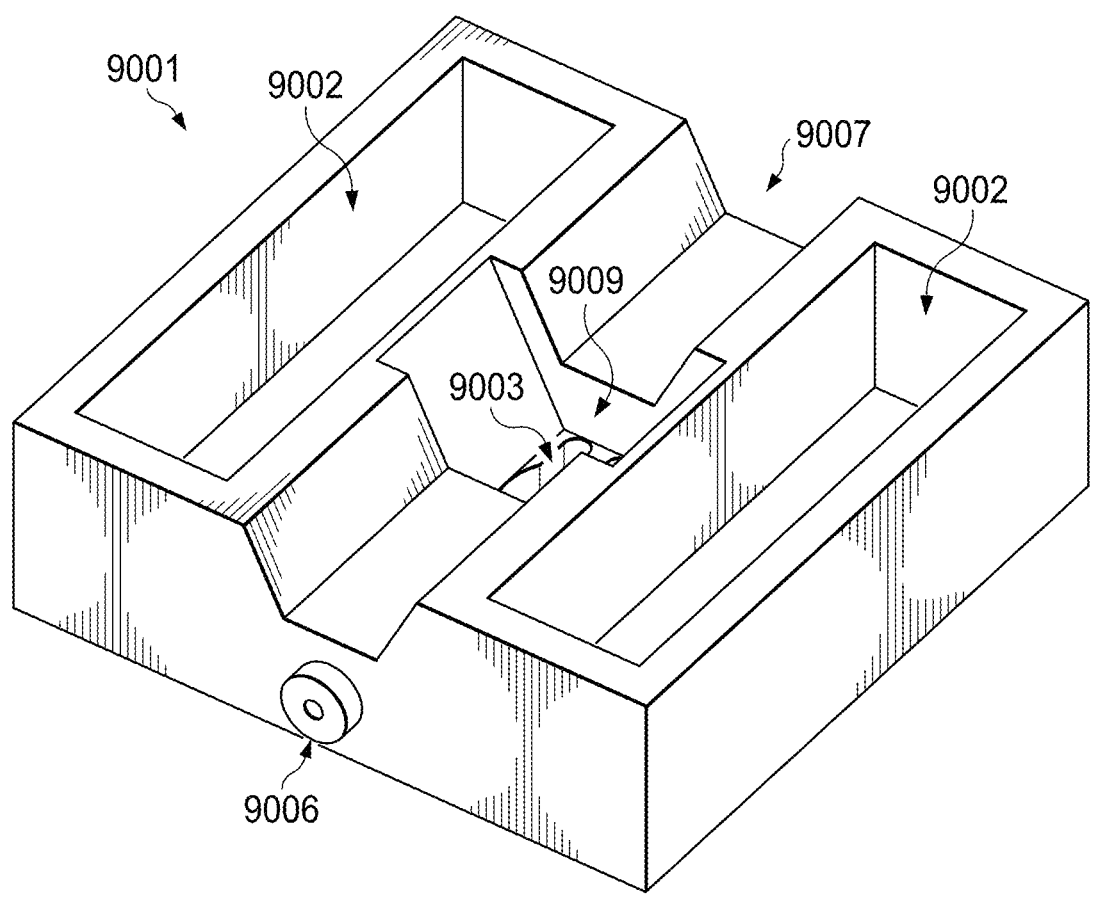
FIG. 11A is a perspective view of a strikethrough plate for acquisition time measurement.
Figure 11B:
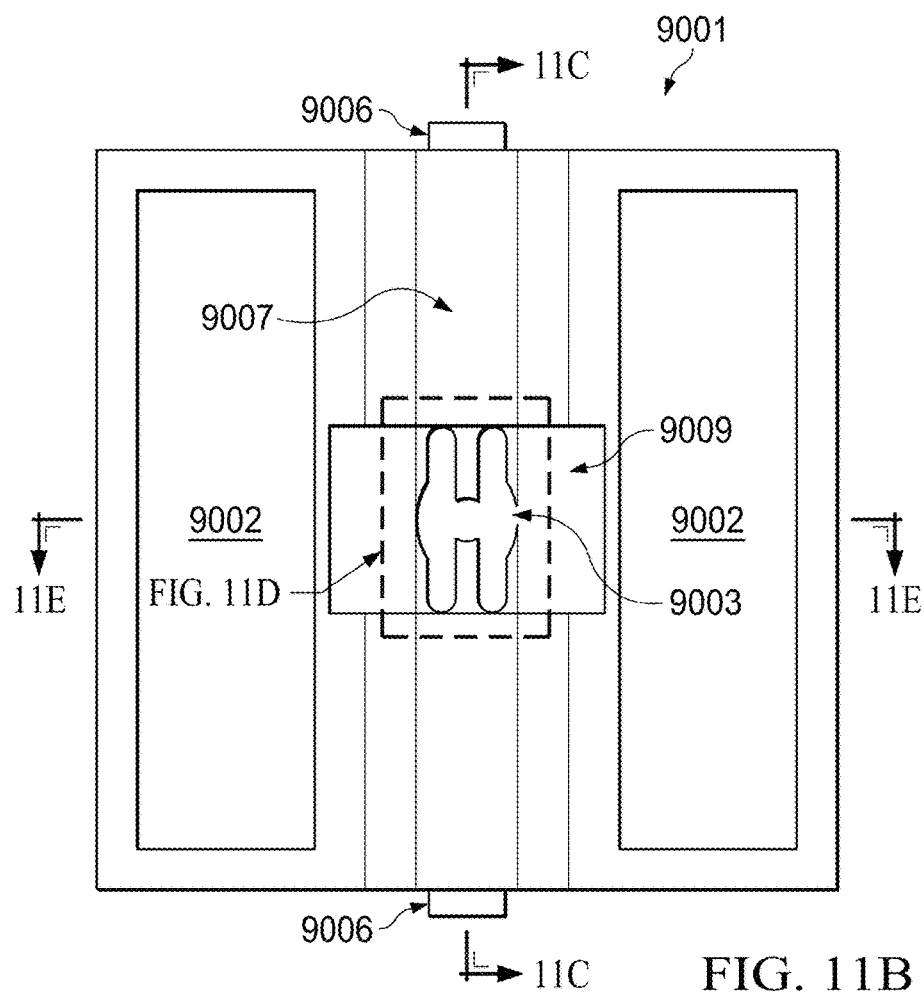
FIG. 11B is a plan view of the strikethrough plate of FIG. 11A.
Figure 11C:
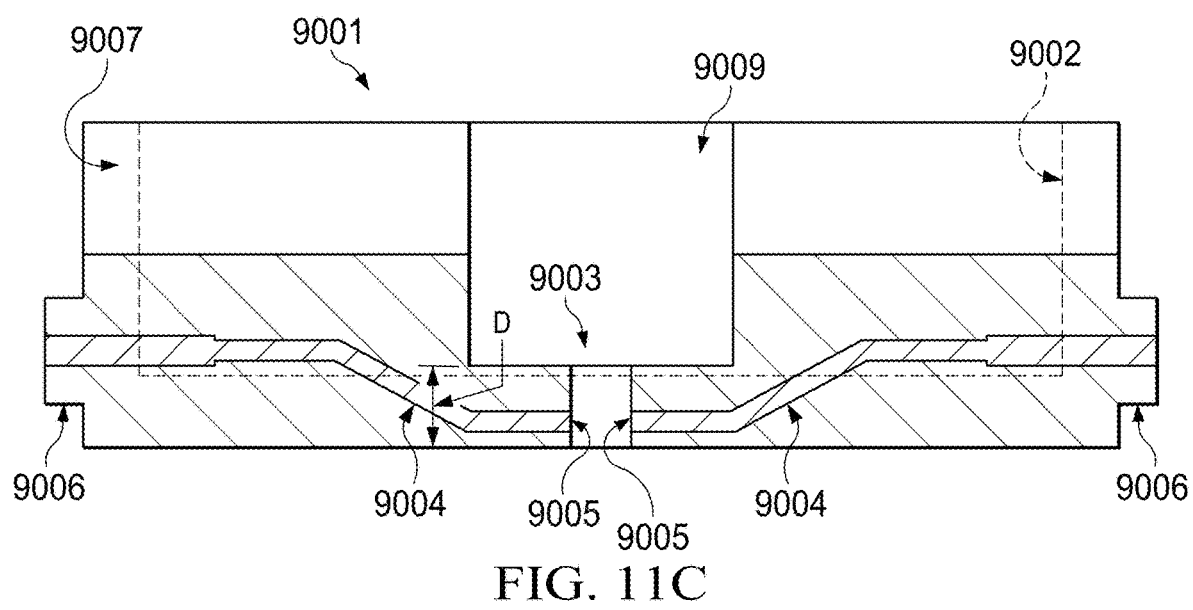
FIG. 11C is a plan view of a 11C-11C direction cross section of the strikethrough plate of FIG. 11B.
Figure 11D:
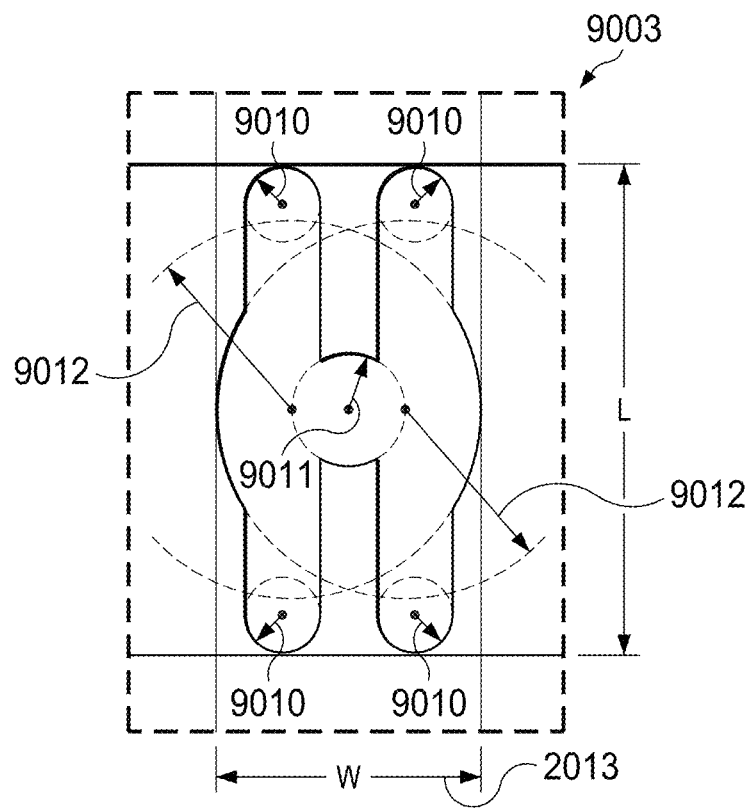
FIG. 11D is a plan view of part pf the strikethrough plate of FIG. 11B.
Figure 11E:
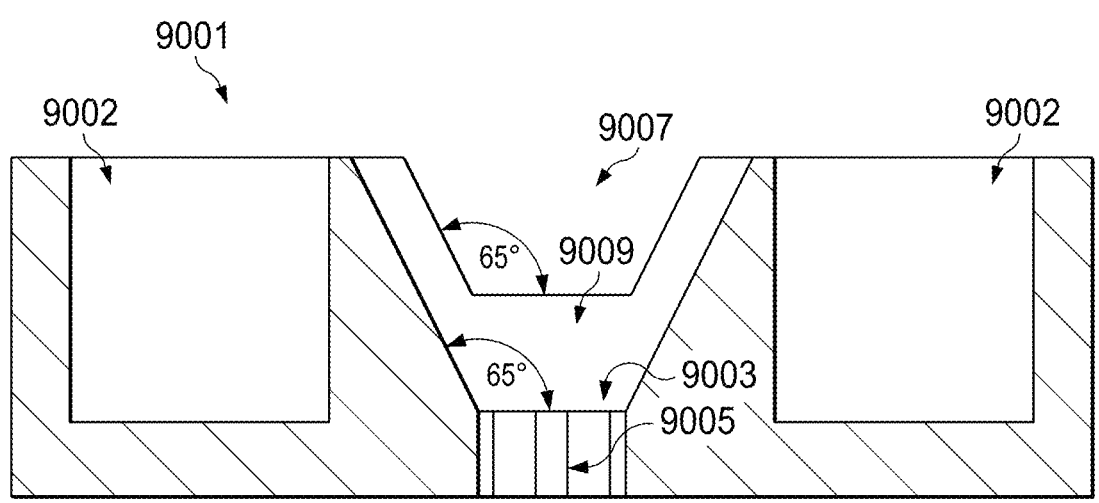
FIG. 11E is a plan view of a 11E-11E direction cross section of the strikethrough plate of FIG. 11B.

Referring to FIGS. 3-5, the first layer 42 of the secondary topsheet 4 has a mean pore size larger than a mean pore size of the topsheet. Preferably, the mean pore size of the first layer 42 is substantially equal to or larger than a mean pore size of the second layer 44 of the secondary topsheet 4.

Topsheet

Referring to FIGS. 1 and 2, an absorbent article of the invention comprises topsheet 1. The topsheet is a layer of the article that contacts the body of the wearer and receives bodily discharges. The topsheet is liquid pervious and may be flexible and non-irritating to the skin. The term "liquid pervious" as used herein refers to components that allow liquids to pass therethrough without significantly retarding or obstructing the transmission of such liquids therethrough.

A topsheet in the present invention can be made by any known or otherwise effective topsheet material, provided that the material has appropriate liquid permeability and smoothness to the skin. The topsheet can be a polymeric film, a nonwoven, a woven fabric, a paper web, a tissue paper web, a cellulosic web or a knitted fabric, or a multi-layer laminate of any of the aforementioned.

Polymeric films suitable for the topsheet can comprise thermoplastic polymers having characteristic rheological properties which depend on their composition and temperature. Polymeric films can include materials normally extruded or cast as films such as polyolefins, nylons, polyesters, and the like. Such films can comprise thermoplastic materials such as polyethylene, low density polyethylene, linear low density polyethylene, polypropylenes and copolymers and blends containing substantial fractions of these materials. Such films can be treated with surface modifying agents to impart hydrophilic or hydrophobic properties, such as imparting a lotus effect. Polymeric films can be textured or otherwise altered by forming macro feature and/or micro features from a strictly flat, planar configuration. As used in the present specification, macro features are elements that are visible to the unaided eye of a person having 20/20 vision from a distance of 30 cm in lighting at least equal to the illumination of a standard 100 watt incandescent white light bulb. Micro features are elements that are not visible to the unaided eye of a person having 20/20 vision from a distance of 30 cm in lighting at least equal to the illumination of a standard 100 watt incandescent white light bulb, wherein the illumination source is within 10 ft and vertically above the viewing surface.

Nonwovens suitable for the topsheet can comprise unbonded fibers, entangled fibers, tow fibers, or the like. Fibers can be extensible and/or elastic, and may be pre-stretched for processing. Fibers of the nonwoven can be continuous, such as those produced by spunbonded methods, or cut to length, such as those typically utilized in a carded process. Fibers can be absorbent, and can include fibrous absorbent gelling materials. Fibers can be bicomponent, multiconstituent, shaped, crimped, or in any other formulation or configuration known in the art for nonwoven webs and fibers.

Nonwovens suitable for the topsheet can be any known nonwovens comprising polymer fibers having sufficient elongation properties to form macro features and/or micro features on the nonwoven.

In some embodiments, the topsheet comprises nonwoven comprising cotton fibers. The topsheet may comprise nonwoven comprising at least 5%, or at least 10, or at least up to 90% of cotton fibers by weigh of the nonwoven. In another embodiment, the topsheet comprises nonwoven of 100% cotton fibers.

In general, the polymeric fibers can be bondable, either by chemical bond (e.g. by latex or adhesive bonding), pressure bonding, or thermal bonding. Nonwovens for the topsheet can comprise about 100% by weight thermoplastic fibers. Nonwovens for the topsheet can comprise as little as about 10% by weight thermoplastic fibers.

A laminate suitable for the topsheet can comprise two or more nonwoven or a combination of polymer films, nonwoven, woven fabrics, paper webs, tissue webs, or knitted fabrics. Not to be limiting, a laminate topsheet can comprise two layers of film, two layers of nonwoven, or a layer of nonwoven with a film.

The topsheet may comprise a plurality of discrete features. Suitable configurations for the features include, but are not limited to, apertures; ridges (continuous protrusions) and grooves (continuous depressions); tufts; columnar shapes; dome-shapes, tent-shapes, volcano-shapes; features having plan view configurations including circular, oval, hour-glass shaped, star shaped, polygonal, polygonal with rounded corners, and the like, and combinations thereof. Such discrete features may be formed according to a known process. When the topsheet is a laminate having a nonwoven, a plurality of discrete features may be formed on either the outermost layer of the laminate, at least two layers of the laminate, or entire layers of the laminate.

Backsheet

Referring to FIGS. 1 and 2, an absorbent article 10 of the invention comprises backsheet 3. The backsheet may be any flexible, liquid resistant, and liquid impervious material. The backsheet prevents discharges collected by and contained in the sanitary napkin, and particularly discharges absorbed by the core, from escaping the sanitary napkin and soiling the clothing and bedding of the wearer. Any conventional backsheet materials may be used within the invention, such as polyolefinic films.

The topsheet and the backsheet are preferentially peripherally joined using known techniques, either entirely so that the entire perimeter of the absorbent article is circumscribed by such joinder or are partially peripherally joined at the perimeter. The term "joined" refers to the condition where a first component is affixed, or connected, to a second component either directly; or indirectly, where the first component is affixed, or connected, to an intermediate component which in turn is affixed, or connected, to the second component. Any joined arrangement that provides for capture of the core intermediate the topsheet and the backsheet and a unitary assembly is suitable.

The backsheet typically extends across the whole of the absorbent structure and can extend into and form part of or all of side flaps, side wrapping elements or wings, when present.

Absorbent Core

Referring to FIGS. 1 and 2, an absorbent article of the invention may comprise an absorbent core 5 disposed between a secondary topsheet 4 and backsheet 3. As used herein, the term "absorbent core" refers to a material or combination of materials suitable for absorbing, distributing, and storing aqueous fluids such as urine, blood, menses, and other body exudates.

The size and shape of the absorbent core can be altered to meet absorbent capacity requirements, and to provide comfort to the wearer. As with the other elements of the articles of the invention, there are no particular requirements for the absorbent core and any standard liquid-absorbent material known in the art for use in absorbent articles will normally be suitable.

Non-limiting examples of liquid-absorbent materials suitable for use as the absorbent core include comminuted wood pulp which is generally referred to as airfelt; creped cellulose wadding; absorbent gelling materials including super-absorbent polymers such as hydrogel-forming polymeric gelling agents; chemically stiffened, modified, or cross-linked cellulose-based fibers; meltblown polymers including co-form; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof. The core, like the article itself, may be generally planar, i.e. does not have a significant variation in thickness.

The fibrous element of the present invention may be directly incorporated into an absorbent core during core making process. For example, when the absorbent core is thin and comprises super absorbent materials, the fibers may be added to the core in a similar way that the super absorbent materials are added. For example, when the absorbent core comprises pulp, the fibers may be added during pulp disintegration process.

Secondary Topsheet

Referring to FIGS. 1 and 2, an absorbent article 10 of the present invention comprises a secondary topsheet 4 disposed between a topsheet 1 and a backsheet 3, or between a topsheet 1 and an absorbent core 5 when it exists.

The purpose of a secondary topsheet is normally to readily transfer the acquired body fluid from a topsheet to an absorbent core, the transfer of fluid occurring not only vertically in the thickness of the secondary topsheet, but also along the length and the width directions of the absorbent product. This helps the fluid capacity of the underlying storage layer to be fully utilized.

Still referring to FIGS. 1 and 2, the secondary topsheet 4 comprises a first layer 42 and a second layer 44, and the first layer 42 is located between topsheet 1 and the second layer 44 of the secondary topsheet 4. In some embodiments, the secondary topsheet is formed by an integrated web. An integrated web herein intends to mean that the first layer 42 and the second layer 44 are bonded by pressure and/or thermo-bond between fibers in the first layer 42 and the secondary layer 44. The first layer 42 and the second layer 44 in the secondary topsheet 4 may be bonded to each other without using chemicals such as adhesive and latex. In the embodiments, at least part of fibers of the second layer 44 may extend into the first layer 42.

A secondary topsheet may be manufactured from a wide range of materials such as woven, nonwoven materials, polymeric materials such as apertured formed thermoplastic films, apertured plastic film, hydro formed thermoplastic films, porous foams, reticulated foams, reticulated thermoplastic films and thermoplastic scrims. Any material described hereinbefore for the topsheet can be used for the secondary layer. In some embodiment A basis weight of the secondary topsheet is in the range of from about 30 gsm to about 100 gsm, or from about 50 gsm to about 95 gsm, or from about 70 gsm to about 85 gsm.

The first layer 42 has a mean pore size larger than a mean pore size of the topsheet 1. Preferably, the mean pore size of the first layer 42 is substantially equal to or larger than to or a mean pore size of the second layer 44. "Substantially equal to" herein with respect to a mean pore size intends to mean that when a mean pore size of the first layer 42 is within a ±5%, or ±4%, or ±5% difference compared to a mean pore size of the second layer 44, the mean pore size of the first layer 42 is substantially equal to the mean pore size of the second layer 44.

A ratio of the first layer to the second layer in basis weight may be in the range of from about 10 gsm to about 90 gsm to about 90 gsm to about 10 gsm, or about 20 gsm to about 80 gsm to about 80 gsm to about 20 gsm. If the basis weight of the first layer is too small, uniformity of the secondary topsheet may be deteriorated, and the secondary topsheet may not provide sufficient void volume. If the basis weight of the second layer is too small uniformity of the secondary topsheet may be deteriorated and/or fail to provide enough capillary capability to drain fluid from the first layer to an absorbent core. If the basis weight of the first layer or the second layer is too large, it may negatively impact fluid acquisition time to an absorbent core.

In one embodiment, the secondary topsheet is constituted by only the first layer and the second layer. In another embodiment, the nonwoven may include at least one additional fiber layer in addition to the first and second layers between the first layer and the second layer, or below the second layer. A fiber for the additional web layer can be selected from natural fibers such as cotton, silk, wool, hemp, pulp, and the like; reclaimed fibers such as rayon, cupra, and the like; and synthetic fibers such as acrylic-based, polyester-based, polyamide-based, polyolefin-based, and polyurethane-based fibers. Such an additional fiber layer may comprise one or more types of fibers selected from these fibers.

First Layer

The first layer comprise a first fiber. The first layer 42 may be hydrophilic.

The first fiber forming the first layer may have a fiber thickness in the range from about 2 denier to about 9 denier, or from about 3 denier to about 6 denier, or from 4 denier to about 5 denier. The first fiber may have a fiber length less than about 100 mm. The first fiber may be a thermoplastic fiber. The first fiber can be a composite fiber such as PE/PP and PE/PET which can be a core/sheath composite fiber. Use of a composite fiber as the first fiber enables the first layer to have good integrity by having adhesions among fibers.

The first layer may comprise a first fiber and a second fiber. When the first layer comprises a first fiber and a second fiber, at least one of the first and second fiber is a thermoplastic fiber. Or, at least one of the first and second fibers may a composite fiber. In one embodiment, one of the first and second fibers is an eccentric fiber and the other is a concentric fiber. The first and second fibers may have different fiber thickness.

Without being bound by theory, employment of two or more types of fibers may be advantageous to optimize suitable pore size distribution and desirable compression recovery and resiliency of secondary topsheet.

The first fiber and the second fiber may be substantially homogenously distributed in the first layer, and no aggregate of one fiber may not be readily visible to the naked eye when the perpendicular distance between the viewer's eye and the plane of the first layer is about 12 inches.

When at least one of the first and second fibers is a composite fiber, the composite fiber can be a core/sheath composite fiber. A core/sheath composite fiber in the present invention may comprise a core component comprising a resin and a sheath component comprising a thermoplastic resin having a melting point of at least about 20° C. lower than a melting point of the resin of the core component. The core/sheath composite fiber preferably has a fiber length less than about 100 mm.

In some embodiments, the first layer comprises a nonwoven comprising the first fiber. Any nonwoven described hereinbefore for the topsheet can be used for the first layer.

In the core/sheath composite fiber, a composite ratio, that is, a volume ratio of core component/sheath component, is preferably from about 80/20 to about 30/70, more preferably from about 70/30 to about 35/65, and more preferably from about 60/40 to about 40/60. Without being bound by theory, in the core/sheath composite fiber, the core component may principally contribute to a bulkiness (initial thickness) and a bulkiness recovery (compressible thickness) characteristics such as cushiony feel of the nonwoven, and the sheath component may principally contribute to strength and softness of the nonwoven. When the composite ratio is from about 80/20 to about 30/70, preferably about 70/30 to about 35/65, and more preferably from about 60/40 to about 40/60, both excellent strength and softness of the nonwoven and bulkiness recovery characteristics may be achieved. If the volume sheath component is increased, the strength of the resulting nonwoven may increase, but the nonwoven may harden and bulkiness recovery characteristics may be compromised. On the other hand, if the core component is excessive, there may be insufficient bonding points, the strength of the nonwoven may decrease and, as a result, bulkiness recovery characteristics may be negatively affected.

The core/sheath composite fiber may have two-dimensional crimps and/or three-dimensional crimps. Herein, the term "two-dimensional crimp" can be understood mechanical crimping in which the peaks of the crimped fiber are sharply angled. Three-dimensional crimp may refer to crimp where the peaks are curved (wave shaped crimping) or spiral (spiral shaped crimping), crimp where both wave shaped crimping and spiral shaped crimping exist, or crimp where both mechanical crimp and at least one of wave and spiral shape crimps exist. Core/sheath composite fibers having two-dimensional crimps may be cost-effective compared to a composite fiber having three-dimensional crimps.

The core/sheath composite fiber in the present invention may be concentric or eccentric. Eccentrics fibers may provide the nonwoven improved softness. In one embodiment, at least one of the first and second fibers is an eccentric fiber in the first layer of the nonwoven of the present invention is an eccentric fiber.

The core component comprises at least one resin, thermoplastic resin preferably. Resin for the core component preferably includes a polyolefin-based resin such as polypropylene, polymethylpentene, and the like; polyester resins such as polyethylene terephthalate, polybutylene terephthalate, polytrimethylene terephthalate, polyethylene naphthalate, polylactic acid, and copolymers thereof; polyamide-based resins such as nylon 66, nylon 12, nylon 6, and the like; acrylic resin; engineering plastics such as polycarbonate, polyacetal, polystyrene, cyclic polyolefin, and the like; mixtures thereof. For the perspectives of the uniformity of the nonwoven and nonwoven productivity, polyolefin resin, polyester and polyamide-based resin are more preferable. Examples of the polyester include polymers and copolymers such as polyethylene terephthalate, polybutylene terephthalate, polytrimethylene terephthalate, polyethylene naphthalate, polylactic acid. The core component may be selected from the group consisting of polyethylene terephthalate, polybutylene terephthalate, polypropylene, nylon, polyamide, and combinations thereof. Polyethylene terephthalate and polybutylene terephthalate are preferred, and polyethylene terephthalate are more preferred. Alternatively, the core component may comprise only polyester as a polymer component.

The core component may comprise additives other than resin, such as anti-static agents, pigments, matting agents, thermal stabilizers, light stabilizers, flame retardants, antimicrobial agents, lubricants, plasticizers, softeners, antioxidants, ultraviolet absorbers, crystal nucleating agents, and the like. These additives may be included in the core component at an amount that is not more than about 10 mass % of the core component.

The sheath component of the core/sheath composite fiber comprises a thermoplastic resin having a melting point that is at least about 20° C. lower than a melting point of the resin in the core component of the core/sheath composite fiber.

The thermoplastic resin suitable for the sheath component may include resins described with respect to the core component above.

The sheath component may comprise additives other than resin, such as anti-static agents, pigments, matting agents, thermal stabilizers, light stabilizers, flame retardants, antimicrobial agents, lubricants, plasticizers, softeners, antioxidants, ultraviolet absorbers, crystal nucleating agents, and the like. These additives are preferably included in the sheath component at an amount that is not more than about 10 mass % of the entire sheath component.

The first layer 42 optionally comprises cellulose-based fibers less than about 10%, or about 5%, or about 2% by weight of the first layer. The first layer 42 may be free from cellulose-based fibers.

Second Layer

Referring to FIGS. 1 and 2, the second layer 44 of the secondary topsheet 4 is located below the first layer 42 of the secondary topsheet 4. A mean pore size of the second layer 44 of the secondary topsheet 4 may be no larger than a mean pore size of the topsheet 1. A mean pore size of the second layer 44 of the secondary topsheet 4 may be equal to or larger than a mean pore size of the topsheet 1.

The second layer comprise a third fiber. The third fiber may be a thermoplastic fiber. The third fiber be a composite fiber such as PE/PP and PE/PET which can be a core/sheath composite fiber. Use of a composite fiber as the third fiber enables the second layer to have good integrity by having adhesions among fibers.

The second layer may comprise nonwoven comprising the third fiber. Any nonwoven described hereinbefore for the topsheet can be used for the second layer. The second layer may be hydrophilic.

The third fiber may have a fiber thickness in the range from about 1 denier to about 6 denier, or from about 2 denier to about 5 denier, or from 3 denier to about 4 denier. The third fiber may have a fiber length less than about 100 mm.

The second layer may comprises cellulose-based fiber from about 10% to about 99%, or from about 30% to about 80%, or from about 50% to about 70% by weight of the second layer.

In some embodiments, the second layer is substantially formed by 100% cellulose-based fibers. In other embodiments, the second layer comprises a cellulose-based fiber and a thermoplastic fiber.

Without being bound by theory, the presence of cellulose-based fiber in the second layer may improve an acquisition speed and mitigate rewet in an absorbent article of the present invention as it may enable the second layer to drain fluid effectively from the topsheet and the first layer of the secondary topsheet and transfer into an absorbent core when it exists, and the presence of thermoplastic fiber may contribute to forming the structure of the second layer. In some embodiments where both a first layer and a second layer of the secondary topsheet contain cellulose-based fibers, an amount of cellulose-based fibers in the first layer by weight of the first layer is lower than an amount of the cellulose-based fibers in the second layer by weight of the second layer proviso that the first layer comprises cellulose-based fibers.

In another embodiment, the second layer is an airlaid nonwoven.

Manufacturing a Web for Secondary Topsheet

A web for the secondary topsheet of absorbent articles according to the present invention may be manufactured via various process known in the industry.

As one example, a web for the secondary topsheet may be manufactured by a process comprising the steps of forming a first fibrous web comprising a first thermoplastic fiber, forming a second fibrous web comprising a second thermoplastic fiber, forming a complex fibrous web by overlaying the first fibrous web on the second fibrous web, and subjecting the complex fibrous web to compression and/or thermal treatment in order to bond at least portion of the first and the second thermoplastic fibers. The first thermoplastic fiber may or may not the same as the second thermoplastic fiber.

As another example, the web for the secondary topsheet may be manufactured in a continuous process. For example, the process may comprise the steps of forming a first fibrous web comprising a first thermoplastic fiber, forming a second fibrous web comprising a second fiber by overlaying the second fibrous web on the first fibrous web to form a composite fibrous web; and subjecting the complex fibrous web to compression and/or thermal treatment in order to bond at least portion of the first and the second thermoplastic fibers. The first thermoplastic fiber may or may not the same as the second thermoplastic fiber.

The first fibrous web and the second fibrous web may be carded webs such as parallel webs, semi-random webs, random webs, cross-webs, criss-cross webs, and the like, air-laid webs, wet-laid webs, and spunbond webs, and the like. The first and the second fibrous webs may be the same, or different.

The thermal treatment of a complex fibrous web can be conducted using any conventionally known thermal treatment method. Examples of preferable treating process include a thermal treatment apparatus such as a hot air through-type thermal treatment apparatus, a hot air blowing thermal treatment apparatus, an infrared thermal treatment apparatus, or the like. These thermal treatment apparatuses are typically provided with a conveying support for supporting and conveying a fibrous web. Thermal treatment may be performed under conditions such that the sheath components of the first and the core/sheath composite fibers sufficiently melt and/or soften, and bond at a point of contact or intersection of the fibers, and such that crimps of the first and the core/sheath composite fiber does not collapse. For example, the thermal treatment temperature may be from about 120° C. to about 150° C., and preferably from about 128° C. to about 145° C.

Test Methods

Pore Size Measurement

Sample Preparation and MicroCT Scanning

A 4 mm punch is used to physically extract a representative region of an absorbent article. The 4 mm diameter sample is then placed in a sample holder with an inner diameter of 5 mm. The sample is packed in super low absorbing packing material such as styrofoam to prevent motion during the scan. A top surface of the sample should have no compression or minimum compression not to alter a caliper of the sample. The sample holder is then placed in an x-ray scanner such as Scanco mCT50 x-ray scanner (Scanco Medical, Zurich, Switzerland). The scanning was performed under parameters chosen to optimize image quality. For example, with Scanco mCT50 x-ray scanner, the scanning was performed with an energy of 55 KeV, with 3000 projections and an integration time of 5 seconds per projection. The resulting data set is 3400×3400×1864 voxels with attenuation values represented as 16 bit integers. Each voxel has a diameter of 2 microns. A file of the resulting data set is of a proprietary format according to the instrument supplier's instruction, and is referred to as the ISQ file in the following steps.

Image Visualization and Analysis

The objective of the image analysis is to measure a 3-dimensional void cell diameter in a topsheet, a first layer of a secondary topsheet and a second layer of the secondary topsheet in each sample. The ISQ files described above, are read into high end image visualization and analysis platform, for example, Avizo 9.2.0 (FEI, Houston, Tex., USA). Upon inspection of obtained visualized 3-dimensional data, 3 different regions in each of the three layers, that is a topsheet, a first layer of a secondary topsheet and a second layer of the secondary topsheet. For each sample there is therefore 9 subvolumes chosen for measurements of 3-dimensional void size diameter. To make measurements of Porosity and 3D void cell size distribution, the following steps were performed:

1. An automated thresholding algorithm practicing Otsu's method (A Threshold Selection Method from Gray-Level Histograms", Nobuyuki Otsu, 2EEE Transactions On Systems Man, and Cybernetics, VOL. SMC-9, NO. 1, January 1979) was applied to each of the datasets resulting in a binary image (0-1) representing the fibers (1) and void space (0).

2. A void cell diameter is measured according to the method disclosed in a paper published by Tor Hildebrand (T. Hildebrand and P. Rüegsegger, "A new method for the model-independent assessment of thickness in three-dimensional images. *Journal of Microscopy,* 185:67-75, 1996). First, the void space is then fitted with spheres of different sizes, where larger spheres cover up smaller spheres using a software working the method disclosed in the paper, for example, IPL software from Scanco Medical, Zurich, Switzerland). This final tessellation of the void space provides a distribution of spheres that completely cover the void space. The volume weighted mean diameter represents the mean void cell diameter. This is implemented through an image analysis platform, for example Matlab R2016B, (Natick, Mass., USA) as module in Avizo 9.2.0.

3. The resulting measurements are brought into Excel 2013. The values of volume weighted mean diameter of the three regions of each layer are then averaged to produce a single value void cell diameter for that layer. The void cell diameter of the region is a mean pore size of the layer.

Artificial Menstrual Fluid ("AMF") Preparation

AMF is composed of a mixture of defibrinated sheep blood, a phosphate buffered saline solution and a mucous component, and has a viscosity between 7.15 to 8.65 cSt at 23° C.

Viscosity on the AMF is performed using a low viscosity rotary viscometer such as Cannon LV-2020 Rotary Viscometer with UL adapter (Cannon Instrument Co., State College, US) or equivalent. The appropriate size spindle for the viscosity range is selected, and instrument is operated and calibrated as per the manufacturer. Measurements are taken at 23° C.±1° C. and at 60 rpm. Results are reported to the nearest 0.01 cSt.

Defibrinated Sheep Blood

Defibrinated sheep blood with a packed cell volume of 38% or greater collected under sterile conditions (available from Cleveland Scientific, Inc., Bath, Ohio, US) or equivalent is used.

Phosphate Buffered Saline Solution

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. Add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

Mucous Component

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. A successful range of gastric mucin is usually between 38 to 50 grams. To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5° C. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range, then remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1° C.

Allow the temperature of the sheep blood and mucous component to come to 23° C.±1° C. Using a 500 mL graduated cylinder, measure the volume of the entire batch of the mucous component and add it to a 1200 mL beaker. Add an equal volume of sheep blood to the beaker and mix thoroughly. Using the viscosity method previously described, ensure the viscosity of the AMF is between 7.15-8.65 cSt. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1° C. Any unused portion is discarded after testing is complete.

Acquisition Time Measurement

Acquisition time is measured for an absorbent article loaded with Artificial Menstrual Fluid (AMF) as described herein, using a strikethrough plate and an electronic circuit interval timer. The time required for the absorbent article to acquire a dose of AMF is recorded. All measurements are performed in a laboratory maintained at 23° C.±2° C. and 50%±2% relative humidity.

Referring to FIGS. 11A-11E, the strikethrough plate 9001 is constructed of Plexiglas with an overall dimension of 10.2 cm long by 10.2 cm wide by 3.2 cm tall. A longitudinal channel 9007 running the length of the plate is 13 mm deep and 28 mm wide at the top plane of the plate, with lateral walls that slope downward at 65° to a 15 mm wide base. A central test fluid well 9009 is 26 mm long, 24 mm deep and 38 mm wide at the top plane of the plate with lateral walls that slope downward at 65° to a 15 mm wide base. At the base of the test fluid well 9009, there is an "H" shaped test fluid reservoir 9003 open to the bottom of the plate for the fluid to be introduced onto the underlying article. The test fluid reservoir 9003 has an overall length ("L") of 25 mm, width ("W") of 15 mm, and depth ("D") of 8 mm. The longitudinal legs of the reservoir are 4 mm wide and have rounded ends with a radius 9010 of 2 mm. The legs are 3.5 mm apart. The central strut has a radius 9011 of 3 mm and houses the opposing electrodes 9004 6 mm apart. The lateral sides of the reservoir bow outward at a radius 9012 of 14 mm bounded by the overall width, W, of 15 mm Two wells 9002 (80.5 mm long×24.5 mm wide×25 mm deep) located outboard of the lateral channel, are filled with lead shot to adjust the overall mass of the plate to provide a constraining pressure of 0.25 psi (17.6 gf/cm$^2$) to the test area. Electrodes 9004 are embedded in the plate 9001, connecting the exterior banana jacks 9006 to the inside wall of the fluid reservoir 9003. A circuit interval timer is plugged into the jacks 9006 to the inside wall 9005 of the fluid reservoir 9003. A circuit interval timer (not shown in the drawings) is plugged into the jacks 9006, and monitors the impedance between the two electrodes 9004, and measures the time from introduction of the AMF into reservoir 9003 until the AMF drains from the reservoir. The timer has a resolution of 0.01 sec.

Test products are removed from all packaging using care not to press down or pull on the products while handling. No attempt is made to smooth out wrinkles. The test samples are conditioned at 23° C.±2° C. and 50%±2% relative humidity for at least 2 hours prior to testing.

The required mass of the strikethrough plate must be calculated for the specific dimensions of the test article such that a confining pressure of 1.72 kPa is applied. Determine the longitudinal and lateral midpoint of the article's absorbent core. Measure and record the lateral width of the core to the nearest 0.1 cm. The required mass of the strikethrough plate is calculated as the core width multiplied by strikethrough plate length (10.2 cm) multiplied by 17.6 gf/cm$^2$ and recorded to the nearest 0.1 g. Add lead shot to the plate to achieve the calculated mass.

Connect the electronic circuit interval timer to the strikethrough plate 9001 and zero the timer. Place the test product onto a flat, horizontal surface with the body side facing up. Gently place the strikethrough plate 9001 onto the center of the test product ensuring that the "H" shaped reservoir 9003 is centered over the test area.

Using a mechanical pipette, accurately pipette 3.00 mL±0.05 mL of AMF into the test fluid reservoir 9003. The fluid is dispensed, without splashing, along the molded lip of the bottom of the reservoir 9003 within a period of 3 seconds or less. After the fluid has been acquired, record the acquisition time to the nearest 0.01 second. Thoroughly clean the electrodes 9004 before each test.

In like fashion, a total of three (3) replicate samples are tested for each test product to be evaluated. Report the Acquisition Time (sec) as the mean of the replicates to the nearest 0.01 sec.

Light Pressure Rewet

Light pressure rewet is measured for an absorbent article loaded with Artificial Menstrual Fluid (AMF) as described herein. The fluid amount left on topsheet, i.e. rewet under 0.1 psi pressure is measured after 3.0 gram and 12.0 gram AMF is dispensed. All measurements are performed in a laboratory maintained at 23° C.±2° C. and 50%±2% relative humidity. Test products are removed from all packaging using care not to press down or pull on the products while handling. No attempt is made to smooth out wrinkles. The test samples are conditioned at 23° C.±2° C. and 50%±2% relative humidity for at least 2 hours prior to testing.

The required mass (to the nearest 0.01 gram) of the plate must be calculated for the specific dimensions of the test article such that a confining pressure of 0.1 psi pressure is applied. Determine the longitudinal and lateral midpoint of absorbent article. Measure and record the lateral width of the absorbent article to the nearest 0.1 cm.

Place the test product onto a flat, horizontal surface with the body side facing up. Place a test vial on a balance, zero it. Use a pipette to add 3.00 gram into the vial and weigh to the nearest 0.01 gram. Then carefully dispense the fluid onto the center of the test articles. Wait for 3 min.

Place 4-6 pieces of known weight filter paper (termed as "dry weight") (a typical lab filter paper, for example, Ahlstrom #632 12.7 cm×12.7 cm filter papers) on top of the center fluid area. Apply the required mass to generate 0.1 psi pressure, keep it under pressure for 5 seconds.

Weigh the filter papers again (termed as "wet weight"). The difference between the wet weight and dry weight of the filter paper is the light pressure rewet at the added amount of fluid.

Repeat the test step till 12.00 gram fluid are dispensed on the absorbent article.

In like fashion, a total of three (3) to six (6) replicates samples are tested for each test product to be evaluated. Report the light pressure rewet as the arithmetic mean of the replicates to the nearest 0.01 gram.

Cross-Section Image

1) Cut a 1 cm×5 cm sample for image-taking at a center area of a sanitary napkin with all the layers of the sanitary napkin remaining.

2) Attach the sample on a metal block with a topsheet-side up.

3) Place the sample with the metal block on a platform of a macroscope, for example, VR-3000 (Keyence, USA) with the cut side in the sample facing to a camera.

4) Focus on the sample, and take a photo from the view of the camera of the macroscope.

EXAMPLES

Example I. Sample Preparation

Sanitary napkins of samples 1-3 as exemplary absorbent articles of the present invention were fabricated using various topsheets and secondary topsheets as indicated in Table 1 and a common absorbent core and a backsheet. Sanitary napkins of comparative samples 1-5 were also prepared using topsheets and secondary topsheets indicated in Table 1 and the same absorbent core and a backsheet as for samples 1-3.

Cross sections of the sanitary napkins were taken according to Cross-section Image under TEST METHODS using VR-3000 Macroscope (Keyence, USA) and VR-3000 software. FIGS. 3-5 are macroscopic images of samples 1-3, respectively. FIGS. 6-10 are macroscopic images of comparative samples 1-5, respectively. It was observed in FIGS. 3-5 that the first layer 42 of the secondary topsheet 4 was more porous than the topsheet 1. It was also observed that the first layer 42 of the secondary topsheet 4 was more porous than the second layer 44 of the secondary topsheet 4.

Example II. Acquisition Time and Rewet

Sanitary napkins of samples 1-3 and comparative samples 1-5 were evaluated as described below. Mean pore size of topsheets, the first and second layers of secondary topsheets were measured according to Pore Size Measurement under TEST METHODS above, and results are indicated in Table 1. Acquisition time and rewet of each sample were measured according to Acquisition Time Measurement, and Right Pressure Rewet under TEST METHODS above, respectively, and results are indicated in Table 1.

extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

TABLE 1

|  |  | Sample 1 | Sample 2 | Sample 3 | Com. Sample 2 | Com. Sample 3 | Com. Sample 4 |
|---|---|---|---|---|---|---|---|
| Topsheet |  |  |  | 40 gsm 100% cotton |  |  |  |
| Secondary topsheet (1$^{st}$ layer/2$^{nd}$ layer) |  | 20 gsm nonwoven*1/ 60 gsm airlaid*2 | 35 gsm nonwoven*3/ 50 gsm airlaid*4 | 55 gsm nonwoven*5/ 40 gsm airlaid*6 | 55 gsm spunlace*7 | 77 gsm airlaid*8 | 50 gsm nonwoven*9 |
| Mean pore size (μm) | topsheet | 66 | 79 | 96 |  | 67 | 43 |
|  | 1$^{st}$ layer | 85 | 175 | 207 |  | 65 | 84 |
|  | 2$^{nd}$ layer | 86 | 97 | 95 |  | n/a | n/a |
| Acquisition time (sec) |  | 75 | 31 | 20 | 133 | 196 | 61 |
| Rewet (g) at 3 g |  | 0.04 | 0.06 | 0.09 | 0.22 | 0.03 | 0.10 |
| Rewet (g) at 12 g |  | 0.40 | 0.42 | 0.53 | 0.95 | 0.43 | 0.82 |

|  |  | Com. Sample 1 | Com. Sample 5 |
|---|---|---|---|
| Topsheet |  | 50 gsm nonwoven*9 |  |
| Secondary topsheet (1$^{st}$ layer/2$^{nd}$ layer) |  | 20 gsm nonwoven*1/ 60 gsm airlaid*2 | 55 gsm spunlace*8 |
| Mean pore size (μm) | topsheet | 91 | 84 |
|  | 1$^{st}$ layer | 78 |  |
|  | 2$^{nd}$ layer |  | 68 |
| Acquisition time (sec) |  | 52 | 88 |
| Rewet (g) at 3 g |  | 0.02 | 0.03 |
| Rewet (g) at 12 g |  | 0.53 | 0.41 |

*$^{1}$2 denier PE/PET concentric fiber, 38 mm
*$^{2}$45 gsm treated pulp, 14 gsm 2.2 dtex PE/PET concentric fiber (3 mm) and 1 gsm latex
*$^{3}$80% 4 denier PE/PP concentric fiber and 20% 4.3 denier PE/PET eccentric fiber, 38 mm
*$^{4}$40 gsm non-treated pulp, 9 gsm 2.2 dtex PE/PET concentric fiber (3 mm) and 1 gsm latex
*$^{5}$80% 6 denier PE/PP concentric fiber and 20% 9 denier PET, 38 mm
*$^{6}$31 gsm non-treated pulp, 8 gsm 2.2 dtex PE/PET concentric fiber (3 mm) and 1 gsm latex
*$^{7}$40% viscose 1.7 dtex (40 mm), 40% PE/PP concentric fiber 1.7 dtex (40 mm) and 20% PET fiber 4.4 dtex (40 mm)
*$^{8}$50% non-treated pulp, 22% PE powder, 22% spunbond nonwoven and 6% latex
*$^{9}$Carded nonwoven, 78% 2D PE/PET and 12% 6D PET The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the

What is claimed is:

1. An absorbent article comprising a liquid permeable topsheet, a liquid impermeable sheet, an absorbent core disposed between the topsheet and the backsheet, and a secondary topsheet disposed between the topsheet and the absorbent core, wherein the secondary topsheet comprises a first layer and a second layer, the first layer being located between the topsheet and the second layer, wherein a mean pore size of the first layer is larger than a mean pore size of the topsheet;

wherein the mean pore size is determined by the pore size measurement method defined in the test methods section herein.

2. The absorbent article according to claim 1, wherein a mean pore size of the first layer is substantially equal to or larger than a mean pore size of the second layer.

3. The absorbent article according to any of the preceding claims, wherein the topsheet comprises nonwoven.

4. The absorbent article according to any of the preceding claims, wherein the topsheet comprises cotton fibers.

5. The absorbent article according to any of the preceding claims, wherein the topsheet comprises at least 5% of cotton fibers by weight of the topsheet.

6. The absorbent article according to any of the preceding claims, wherein the topsheet comprises 100% cotton fibers by weight of the topsheet.

7. The absorbent article according to any of the preceding claims, wherein the secondary topsheet is an integrated web.

8. The absorbent article according to any of the preceding claims, wherein at least part of fibers of the second layer extended into the first layer.

9. The absorbent article according to any of the preceding claims, wherein the first layer comprises a first thermoplastic fiber.

10. The absorbent article according to any of the preceding claims, wherein the second layer comprises at least about 10% cellulose-based fibers by weight of the second layer.

11. The absorbent article according to claim 10, wherein the cellulose-based fibers are selected from the group consisting of cotton, hemp, pulp and rayon, cupra, and combinations thereof.

12. The absorbent article according to any of the preceding claims, wherein the second layer comprises a second thermoplastic fiber.

13. The absorbent article according to any of the preceding claims, wherein the first layer comprises nonwoven.

14. The absorbent article according to any of the preceding claims, wherein the first layer comprises a first fiber and a second fiber, wherein a fiber thickness of the first fiber differs from a fiber thickness of the second fiber.

15. The absorbent article according to any of the preceding claims, wherein the first layer and the second layer are hydrophilic.

16. The absorbent article according to any of the preceding claims, wherein the first layer comprises less than about 10% cellulose-based fibers by weight of the second layer.

17. The absorbent article according to any of claims 1-15, wherein the first layer is free from cellulose-based fibers.

18. The absorbent article according to claim 16, wherein an amount of cellulose-based fibers in the first layer by weight of the first layer is lower than an amount of the cellulose-based fibers in the second layer by weight of the second layer proviso that the first layer comprises cellulose-based fibers.

19. The absorbent article according to any of the preceding claims, wherein a weight ratio of the first layer to second layer is in the range of from about 1:9 to about 9:1.

* * * * *